United States Patent [19]

Jeffers

[11] Plant 4,864

[45] Jul. 6, 1982

[54] RED MAPLE

[76] Inventor: Glenn C. Jeffers, 700 Susan Dr., Fostoria, Ohio 44830

[21] Appl. No.: 171,647

[22] Filed: Jul. 23, 1980

[51] Int. Cl.[3] ..... A01H 5/00
[52] U.S. Cl. ..... Plt./51
[58] Field of Search ..... Plt./51

[56] References Cited

U.S. PATENT DOCUMENTS

P.P. 3,817 12/1975 Flemer ..... Plt./51

*Primary Examiner*—James R. Feyrer
*Attorney, Agent, or Firm*—Maky, Renner, Otto & Boiselle

[57] ABSTRACT

A new and distinct variety of red maple tree, characterized by its upward habit of growth and good crotch angles; rapid growth rate; tolerance to drought conditions; pleasing lettuce green summer leaf color and excellent scarlet fall leaf color that persists.

2 Drawing Figures

1

The present invention or discovery relates to a new and distinct variety of red maple tree, *Acer rubrum,* originated by me, having a novel habit of growth and other distinguishing characteristics as will be hereinafter more particularly pointed out. The original parent specimen was a seedling grown by me at Fostoria, Ohio, and such original plant specimen was discovered and selected by me from a plantation of red maple seedlings grown by me from seed.

This new variety of red maple tree is a well formed tree of very rapid growth, good crotch angles, and drought resistant. The novel and distinctive features of this new variety are considered to be, in combination:

1. The upright habit of growth with good crotch angles.
2. Very rapid growth rate compared to other red maple trees.
3. Tolerance to drought conditions.
4. Pleasing lettuce green summer leaf color and excellent scarlet fall leaf color that persists.

There is a large demand for rapid growing trees for landscape planning, and red maple trees have been recognized for a long period of time as being especially suitable for such purposes. My new red maple tree exhibits an unusual combination of excellent fall color, drought resistance, and good crotch angles. Also, the original tree, which is approximately twelve years old, has never fruited to date, and no blossoms have been observed. This new variety has been propagated asexually at Gresham, Oreg., by budding and from cuttings, and such progeny demonstrate the same novel characteristics.

The accompanying drawing shows the parent tree in full fall color, as well as the outline of a typical leaf shape.

The following is a specific description of such new variety, the color terminology being taken from the Royal Horticulture Society Color Chart.

The original tree has never fruited as aforesaid, and has never been sprayed since it has never had any disease or insect problem. The original tree is out in the open, yet no branches have ever broken, and such tree has failed to suffer from drought when other red maple trees showed severe stress under substantially the same drought conditions.

2

The average crotch angle of typical lateral branches of my new red maple tree growing at the Seacrest Arboretum in Wooster, Ohio is 58° measured from the vertical. By contrast, the average crotch angle of the known, marketed cultivar Red Sunset also growing at the Seacrest Arboretum is 44°.

The original plant, at about twelve years old, has a trunk diameter of 7 inches at 18 inches from the ground. The side branches are upright and the twigs are cherry-color plate 722 of the Royal Horticulture Society Color Chart.

Both the original plant and the progeny therefrom show a similar rapid rate of growth, with four year old progeny measuring $1\frac{3}{4}$ inches in diameter at 18 inches from the ground. The average terminal growth of such four year old progeny growing at the Seacrest Arboretum in Wooster, Ohio for the last three years is as follows:

For the year 1979 — 2 feet
For the year 1980 — 1 foot $4\frac{1}{2}$ inches
For the year 1981 — 2 feet 5 inches By contrast, the average growth rate over the same period of time of the red maple species Red Sunset planted at the Seacrest Arboretum in 1967, which is the youngest cultivar of red maple trees also growing there under the same cultural conditions, is as follows:

For the year 1979 — $7\frac{1}{2}$ inches
For the year 1980 — 1 foot $1\frac{3}{4}$ inches
For the year 1981 — 1 foot $1\frac{1}{4}$ inches The leaves are thick and leathery and are cut and have five lobes that are pointed. The leaves are generally of the shape shown in the drawing and have an average blade length along the longitudinal center of approximately $2\frac{3}{4}$ inches to 3 inches and average width at the widest center portion of the leaf of approximately 3 inches to $3\frac{1}{4}$ inches.

The summer leaf color is a pleasing lettuce green-color plate 861. The color of the leaves in full fall color is predominantly scarlet-color plate 19, ranging to chrome yellow-color plate 605 Slash No. 1. The length of fall color will vary with locale and season variation from year to year. In the fall of 1980, in Fostoria, Ohio, on average the fall leaf color started around the 14th of October and lasted until leaf fall around the 24th of October.

In view of its upright habit of growth with good crotch angles, drought resistance, pleasing summer color and excellent fall color that persists, my new red maple tree is particularly well suited for use in landscape planning.

I claim:

1. A new and distinct variety of red maple tree, *Acer rubrum,* substantially as described and illustrated, characterized by its upward habit of growth and good crotch angles; rapid growth rate; tolerance to drought conditions; pleasing lettuce green summer leaf color and excellent scarlet fall leaf color that persists.

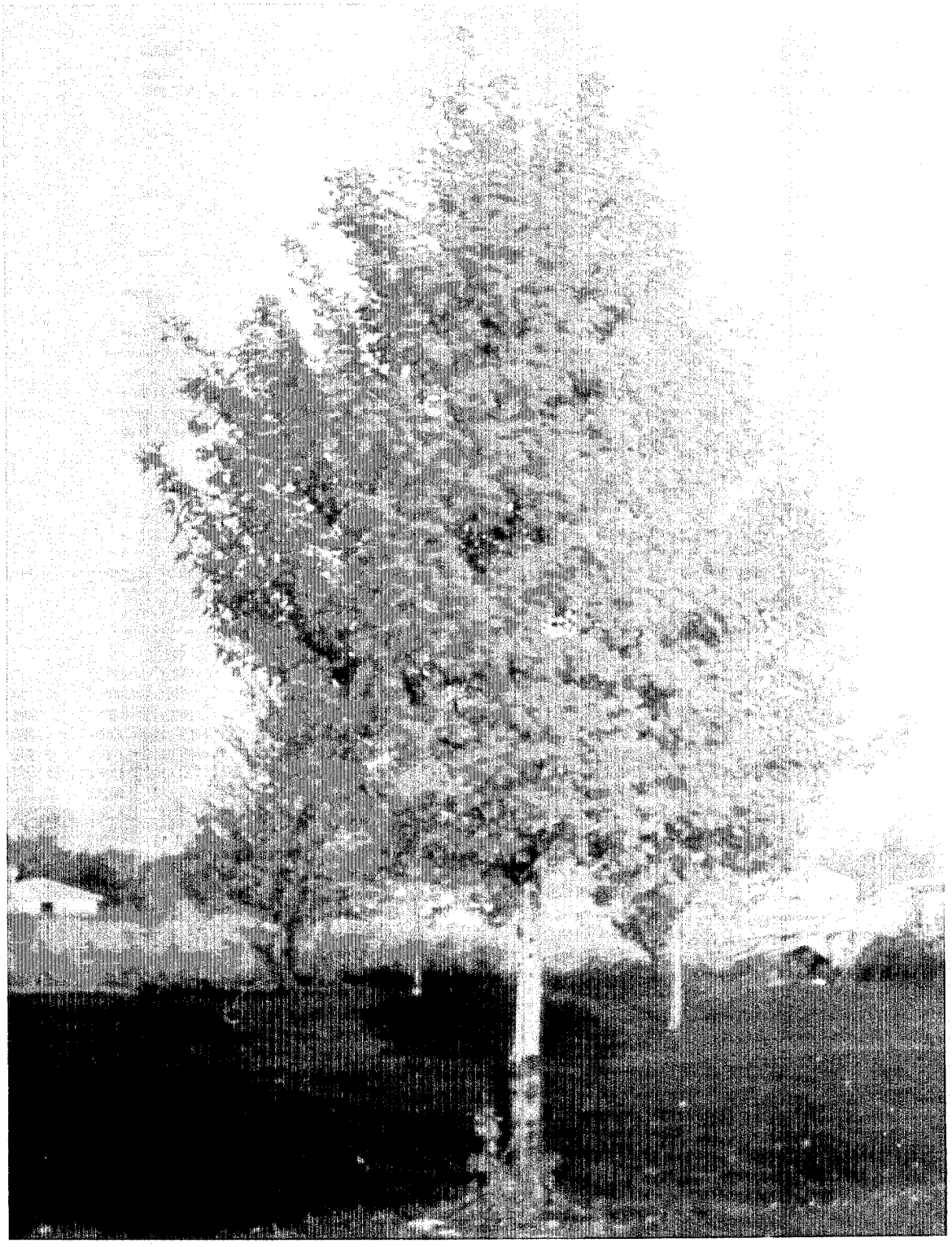

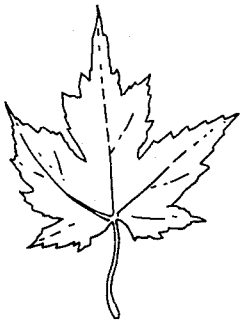

* * * * *